United States Patent [19]

Lundblad

[11] Patent Number: 4,539,978

[45] Date of Patent: Sep. 10, 1985

[54] APPARATUS FOR TREATING BACK AILMENTS

[76] Inventor: Leif Lundblad, Häradsvägen 102, S-141 41 Huddinge, Sweden

[21] Appl. No.: 474,648

[22] PCT Filed: Aug. 19, 1982

[86] PCT No.: PCT/SE82/00263

§ 371 Date: Feb. 9, 1983

§ 102(e) Date: Feb. 9, 1983

[87] PCT Pub. No.: WO83/00620

PCT Pub. Date: Mar. 3, 1983

[30] Foreign Application Priority Data

Aug. 21, 1981 [SE] Sweden ............................... 8104962

[51] Int. Cl.[3] ............................................... A61F 5/00

[52] U.S. Cl. ..................................................... 128/71

[58] Field of Search .................................... 128/70-74; 269/322-328

[56] References Cited

U.S. PATENT DOCUMENTS 1,499,013 6/1924 Gunther ............................... 128/72
1,830,071 11/1931 Patton .................................. 128/72
2,690,175 9/1954 Daughtry ............................. 128/71
2,950,715 8/1960 Brobeck ............................... 128/71
3,771,518 12/1973 Greissing ............................. 128/71
4,378,791 4/1983 Sarrell .................................. 128/71

*Primary Examiner*—Robert A. Hafer
*Assistant Examiner*—Arnold W. Kramer
*Attorney, Agent, or Firm*—Sughrue, Mion, Zinn, Macpeak, and Seas

[57] ABSTRACT

An apparatus for treating back ailments includes a support for supporting a patient in a horizontal, lying position on the patient's back. A first tension force take up belt passes about the pelvis of the patient, while a second such belt passes around the chest of the patient. A pulling or tension device is connected to one of the belts so as to move relative to the support. A carriage moves with the support but with slight friction and carries either the pelvis or chest of the patient to exhibit a high degree of friction against the tension device. The small of the back is supported by a moveable member, and the carriage executed simultaneously with or independently of translatory movement relative to the support, rotary movement substantially in the horizontal plane or a skewing or distorting movement about an axis extending substantially parallel to the longitudinal direction of the carriage in accordance with a predetermined program.

5 Claims, 8 Drawing Figures

APPARATUS FOR TREATING BACK AILMENTS

TECHNICAL FIELD

The present invention relates to apparatus for treating back ailments. The apparatus is of the kind which incorporates support means for supporting a patient in a horizontal, lying position; a first tension take-up means arranged to pass around the pelvis area of the patient, tensioning means connected to the first tension take-up means or to a second tension take-up means arranged to pass around the chest area of the patient; and a readily moveable carriage means arranged for movement relative to said support means and intended to support the pelvis of the patient.

BACKGROUND ART

Apparatus are known for treating people with back ailments by means of traction and torsion. One such known apparatus includes a rotatably arranged support for the patient's chest and head; a raisable and lowerable support means arranged for rotation about its axis and intended for supporting the small of the back of a patient; and a longitudinally displaceable support means for supporting the pelvis and legs of the patient.

Another known apparatus includes head/chest supports; means for supporting the small of the back, the pelvis and the legs of a patient, with the leg support means arranged for repeated rotary movement in a vertical direction and the means for supporting the small of the back and the pelvis being arranged for rotary movement about a horizontal axis irrespective of the movement of the leg support means. Although these and other similar apparatus permit certain controlled relative movement between the pelvis area and chest area of a patient, there is still a need for apparatus which are more flexible in operation and which can be adapted more readily to the individual requirements of different patients undergoing treatment.

DISCLOSURE OF THE INVENTION

When using an apparatus constructed in accordance with the invention the back of a patient can be treated three-dimensionally in a controlled fashion, namely by traction, torsion about a vertical axis and distortion about a horizontal axis, and treatment can be carried out without requiring the patient to be moved. The treatment should initially be carried out once a day, to be later followed by a more gentle traction mode over a longer period of time and while resting, for example during the night.

The apparatus can be designed so that the patient himself is able to carry out each individual movement manually and in a controlled fashion, in accordance with the doctor's orders.

In accordance with a further embodiment of the apparatus according to the invention the means for supporting the small of the back automatically protects the back from being overstrained and the loin part of the back from being wrongly angled when the patient is subjected to traction .

The characterizing features of an apparatus constructed in accordance with the invention are set forth in the following claims.

BRIEF DESCRIPTION OF THE DRAWINGS

The invention will now be described in more detail with reference to the accompanying schematic drawings in which.

PREFERRED EMBODIMENT OF THE INVENTION

Figure 1:
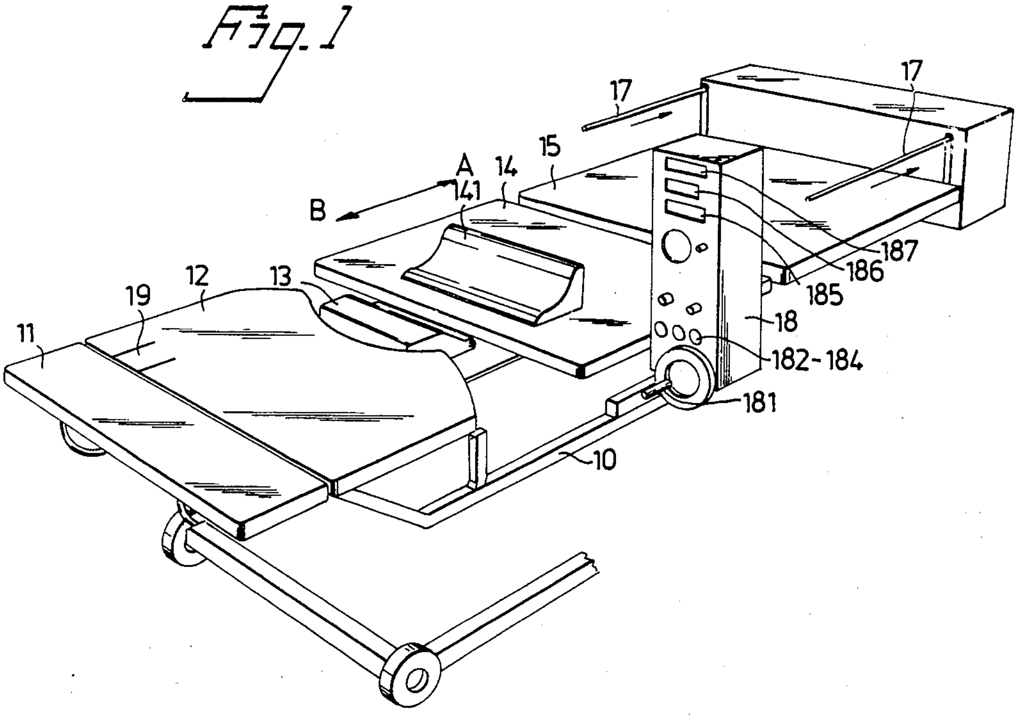
FIG. 1 is a top plan view in perspective of an apparatus according to the invention.

The apparatus illustrated in FIG. 1 comprises support means 10 for supporting a patient in a horizontal, lying position and having arranged thereon a head support 11, back support 12, means 13 for supporting the small of the back, pelvis support means 14 and leg support means 15. Arranged on the back support is a second tension force take-up means (belt) 19 which is only partly shown and which, during treatment, is fixedly arranged relative the support means 10 and intended to pass around the chest region of the patient. The means 13 for supporting the small of the back is vertically displaceable and arranged for movement in the horizontal plane. The pelvis support means 14 has the form of a carriage-like means arranged for movement relative the support means 10 with but slight friction, and is intended to support the pelvis region of the patient. Connected to the pelvis support is a first tension force take-up means (belt) which is not shown in the Figure and which is arranged for movement, together with the pelvis support means, relative to the support means 10 and intended to pass around the pelvis region of the patient. The pelvis support 14 is also provided with a separate, cupped upstanding support 141. Connected to the first tension force take-up means is a pulling means 17, which is indicated in FIG. 1 by two pulling lines and which is intended to move the first tension take-up means relative the support means 10. When drawing in the means 17, the carriage-like means 14 is imparted a translatory movement; when the pulling force is interrupted, the means 14 is returned to its starting position by means of a spring (not shown) arranged in the support means 10. The aforementioned movements are shown by arrows A, B.

Arranged on the right-hand side of the apparatus, so as to be conveniently reached by a patient lying on said apparatus, is an operating unit 18 comprising a crank 181, gear levers 182–184, and instruments 185 and 187 for disclosing the traction force, and the angles of twist or rotation and distortion respectively. The operating or control unit can be swung out, so as to be readily accessible to a doctor or therapist. When the lever 182 is moved to a lower position and the crank 181 turned clockwise, the lines 17 are drawn in and the tension or pulling force exerted can be read-off the instrument 185, within the range of about 0–100 kp.

The pelvis support means (the carriage) 14 and the leg support means 15 are mounted on a support beam which can be rotated about a vertical axis. The beam support, and therewith also the pelvis support means 14 and leg support means 15, is rotated by moving the lever 183 to a lower position and turning the crank 181; the extent to which rotation has been effected, either to the right or to the left, can be read-off from the instrument 186 within an angular range of about 0°–20°. The means 13 for supporting the small of the back is arranged so as to partially accompany the aforementioned rotary movement in the horizontal plane, i.e. will move within an angular range of 0°–10° to the right or to the left.

The pelvis support means (the carriage) 14 and the leg support means 15 are also mounted on a frame arranged to execute a distorsion movement about its longitudinal axis.

Figure 3:
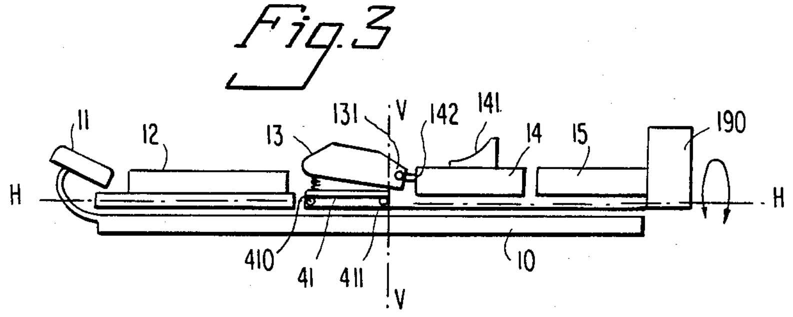
FIG. 3 is a side elevational view which illustrates in smaller scale parts of the apparatus shown in FIG. 1 as seen from the side, with the axes of rotation also illustrated.

The pelvis support means and the leg support means are skewed by moving the lever 184 to a lower position and turning the crank 181; the extent to which skewing is effected in direction NO-SV or NV-SO within a range of about 0°–30° about axis H—H, FIG. 3, can be read-off from instrument 187. The means 13 for supporting the small of the back does not accompany this movement, although the means 13 can be adjusted to the position of the back owing to the fact that the upper part of said means 13 is constructed so as to yield. Preferably, the surface of the means 13 for supporting the small of the back is covered with a friction-reducing material, such as Teflon, so as to be relatively friction free against the small of the patient's back.

The (imaginary) vertical axis about which the aforementioned rotary movement takes place is suitably located between the pelvis support 14 and the means 13 for supporting the small of the back. More specifically, the various means should be adjusted so that the axis of rotation is located approximately in the vicinity of the second vertabra, counted from the pelvis area.

The (imaginary) distorsion or skewing axis about which the aforementioned skewing movement takes place suitably coincides with a concentric axis through three vertabrae of the patient located nearest the pelvis. When mention is made in the aforegoing of a horizontal plane, vertical axis etc., the point of departure is taken with a patient lying horizontally in a "recumbant" position. Should, for some reason or other, the patient be placed in a slightly twisted position, the aforementioned terms must be given a somewhat different meaning, although there should be no difficulty in understanding what is actually meant. These facts have been taken into consideration by incorporating the word "substantially" in the claims.

In order for treatment of a patient on the aforedescribed apparatus to have full effect, it is important that the pelvis portion of the patient is pressed effectively against the carriage-like means 14, thereby ensuring that it accompanies the translatory, twisting and skewing movements carried out by said carriage-like means.

Figure 2:
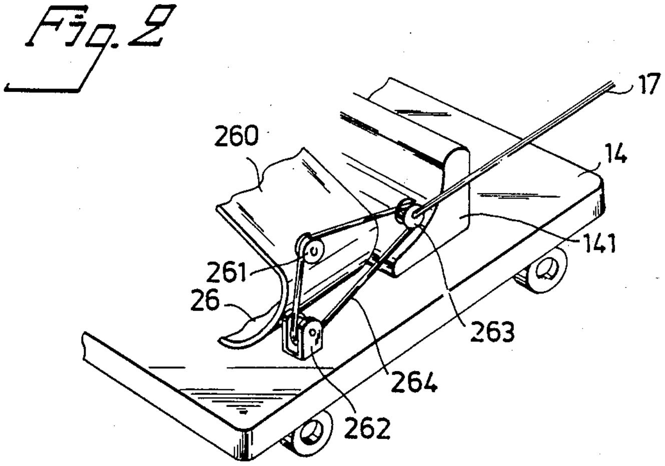
FIG. 2 is a perspective view which illustrates a tension force take-up means incorporated in the apparatus illustrated in FIG. 1.

To this end, the first tension take-up means (the belt 26) is of particular design, see FIG. 2. The member 26 of the illustrated embodiment includes a belt 260, which passes around the pelvis area of a patient, a first wheel or roller 261 attached to the belt 260, a second wheel or roller 262 attached to the carriage-like means 14, a third wheel or roller 263 arranged to be connected to the pulling means 17, and an endless belt, strap or the like 264 which connects the three wheels or rollers, the first wheel or roller 261 being located between the second (262) and the third (263) wheels or rollers at a level which is substantially higher than the second wheel or roller 262. The third wheel or roller 263 is connected to one of the lines 17. On the other (hidden) side of the belt 260 there is provided corresponding wheels or rollers and endless belts or straps, these units being arranged in a corresponding manner and connected to the other line 17. This arrangement ensures that the pelvis of the patient will be effectively pressed downwardly and forwardly onto and against the upstanding support 141 when the lines 17 are pulled in or tensioned, thereby to accompany the various movements of the pelvis support means 14. A certain retaining effect between the chest/back of the patient and the means 13 for supporting the small of the back also contributes to the aforesaid action.

FIG. 3 is a side view of an apparatus according to the invention, illustrating the support means 10 and the supports 11–14. The aforementioned imaginary vertical axis is identified by references V—V, while the imaginary horizonal axis is identified by references H—H. By, for example, suitable cradle construction, the horizontal axis H—H can be adapted to the characteristics of the backs of different patients (whether the small of the back is high or low, etc.).

The described apparatus has the following mode of operation. It is assumed that a doctor has prepared a suitable programme for the patient. The chest belt 19 and the pelvis belt 26 are laid out on the back support means 12 and the pelvis support means 14 respectively, the latter being locked in a normal, starting position. The patient lies down on the support means 11–15, and first tightens the belt 26 and then the belt 19, suitably by means of a crank arrangement arranged to manipulate a roller beneath the back support means 12, whereafter the patient begins with a traction movement, by turning the crank 181 until the instrument 185 shows the traction force ordained by the doctor. (Activation of the crank 181 breaks the locking of the support means 12). After a given length of time has passed, the patient can continue, in the previously described manner, with a rotary movement or a distortion or skewing movement, possibly in combination with traction.

The apparatus can also be provided with means for applying heat and/or vibrating the small of the back, via the support means 13. These functions are also controlled from the control unit 18 by means of separate devices, and are time controlled.

Figure 4A:
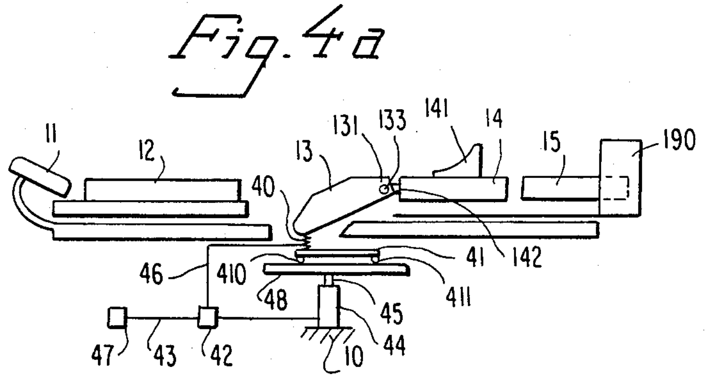
FIG. 4 is a side view of an apparatus according to the invention having pressure-sensing means, FIG. **4*a* is a side view of the apparatus of FIG. 4** with components in modified position.
Figure 4:
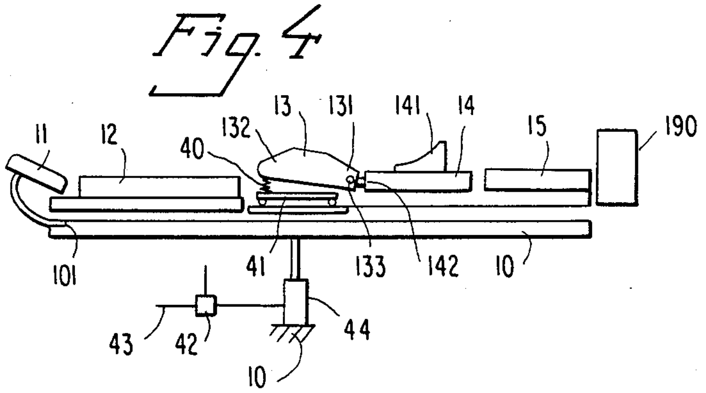

The apparatus illustrated in FIG. 4 is provided with a pressure sensing means 40 of known type, for sensing the pressure of the means 13 for supporting the small of the back, generated by a patient lying on the units 11, 12, 13, 14, 15. The means 13 for supporting the small of the back is rotatably connected through 133 a ball joint to the end 131 of the carriage-like means 14 facing the main end of the apparatus, while the other end 132 of said support means 13 rests against a vertically moveable support plate 41. This support plate can be raised and lowered in dependence upon the aforementioned pressure, and optionally also in relation to a given, individual programme for the patient undergoing treatment.

Figure 5:
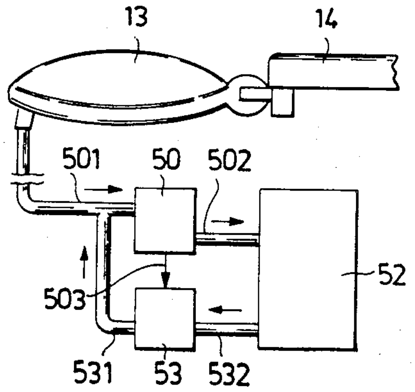
FIG. 5 is a schematic view which illustrates a modified form of part of the apparatus illustrated in FIG. 4.

FIG. 5 illustrates a modification of the apparatus illustrated in FIG. 4. In this embodiment, the means 13 for supporting the small of the back comprises a hollow container filled with pressure medium, liquid or gas, and the pressure means 50 comprises a valve provided with lines 501, 502 for passing pressure medium to the support means 13 and to a magazine 52 for pressure medium, and a control-signal connection 503 to a pump unit 53. The pump unit 53 is provided with an outlet line 531 passing to the support means 13, and an input line 532 passing to the magazine 52.

The pressure means 50 is arranged to control the flow of medium to (via members 532, 53, 531) and from (via members 501, 50, 502) the means for supporting the small of the back, in dependence upon the pressure sensed and optionally also in dependence upon a predetermined pressure-time programme. In addition to a further development of the invention, in addition to the aforementioned control function, the pressure means 50 and the pump unit 53 are also arranged to superimpose a pressure component, so as to obtain a vibratory effect, optionally in conjunction with the supply of heat, so that the pressure medium is heated at the temperature suitable for the patient.

In accordance with another modification in accordance with the invention, the back support means 12 may be moveably arranged, while the pelvis support means 14 (previously referred to as readily moveable carriage means) are fixedly arranged. In this case, the pulling or tension means 17 is instead connected to the back support means 12, i.e. traction is now effected directly in the chest portion of the patient. This means, however, when distorting the back of a patient about a horizontal axis, the back support means 12 and the means 13 for supporting the small of the back must be skewed together relative the pelvis support means 14, which is now fixed, so that the treatment is still concentrated on the first three vartebrae (lowest) of the patient's spine.

The various means for carrying the aforedescribed movements into effect, i.e. the translatory movement in the direction of the arrows A–B, the rotary movement about the vertical axis V—V and the twisting or distortion movement about the horizontal axis H—H, the vertical movement of the support means 13, and the arrangement of support means 14 and 15 in the frame or support 10, are described in the following. The carriage 14, similar to the leg support means 15, is displaceably mounted on rollers 266 (FIG. 2), which in turn, are mounted on a support plate 600. The support plate 600, which in the illustrated embodiment is of oblong shape and provided with longitudinally extending flanges 601 for guiding the rollers 266, is provided with a central stud 602 (FIG. 6), rotatably mounted in a bearing housing 603. The bearing housing 603 is firmly mounted on a central beam 604 in an oblong frame 605, located beneath the plate 600. The two short sides of the frame 605 have two exle-stubs 606 and 607 which are co-axial with one another and which are journalled for free rotation in the frame 10 in a manner not shown in detail.

Thus, the plate 600, and therewith the support means 14 and 15 can be rotated about the vertical axis V—V, while the frame 605, together with the plate 600 and support means 14 and 15, can be rotated about the horizontal axis H—H (FIG. 3). The aforementioned translatory movement of the support means 14 and 15, or optionally solely the support means 14 and the support means 13 connected thereto, is made possible by the illustrated arrangement of the roller path and rollers 266, chosen by way of example only.

As will be seen from FIGS. 3, 4 and 4*a*, one end of the support means 13 is connected by means of a ball joint 131, or the like, to the end 142 of the support means 14, and the other end 132 of the support means 13 is supported by a pressure sensor 40, of any conventional known type. The pressure sensor 40 is, in turn, supported by a support plate 41, which is journalled on rollers or wheels 410, 411 co-acting with a raisable and lowerable table 48. The table 48 is firmly attached to the ram or piston 45 of a piston-cylinder device 44, firmly mounted in the frame 10. In the illustrated embodiment, the pressure sensor 40 is arranged to generate an electric signal corresponding to the pressure on the support means 13, this signal being transmitted to an electrically controlled hydraulic valve 42 via a conductor 46. The hydraulic valve is arranged to feed hydraulic fluid through a line 43 to the cylinder 44 from a source of pressure 47, and to allow said fluid to depart from said cylinder, through said line 43, so as to adjust the piston rod, and therewith the table 48 and the support means 13, to a position corresponding to the pressure exerted by the patient on the support means 13.

Figure 6:
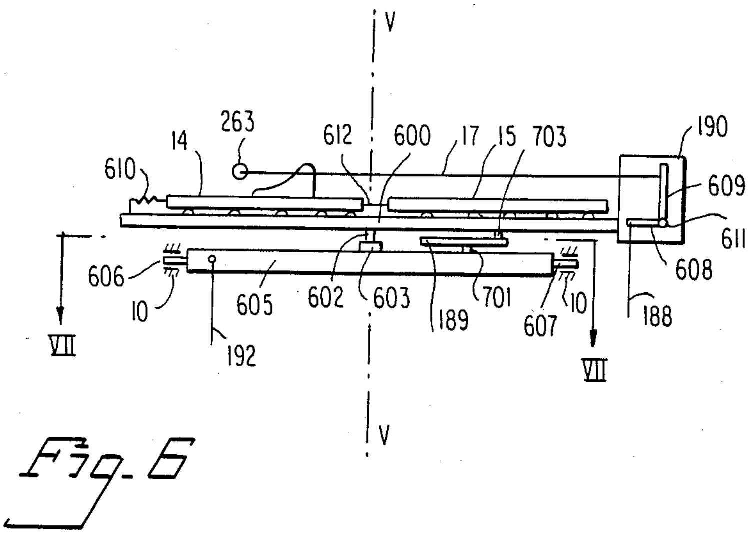
FIG. 6 is a schematic side view of an embodiment of the invention showing in detail the various means for effecting movement of components thereof.

The aforementioned longitudinal movement of the support means 14 is effected by moving the central lever 183 (FIG. 1) to a lower position, and therewith engage the crank 181 with the inner steel-wire of a Bowden-cable 188. Rotation of the crank 181 causes the steel-wire to move axially. As indicated in FIG. 6, the steel-wire is connected to one arm 608 of a double-arm lever, which is freely journalled on a pin 611 in a housing 190. As shown in FIG. 6, an arm 609 which forms an angle of approximately 90 degrees with the arm 608 in the illustrated embodiment has a free end which is connected to the pulling means or line 17, which in turn is connected to the roller 263 (FIG. 2). The housing 190 has arranged therein two such double-arm levers, one for each pulling line 17, although both arms are controlled by the cable 188. It will be seen that when the crank 181 is turned to rotate the arm 608 clockwise about the pin 611, the lines 17 will move the carriage 14 to the right in FIG. 6, while when the arm 608 is rotated anti-clockwise, a tension spring 610, connected at one end to the carriage 14 and at the other end to the plate 600, will cause the carriage 14 and the support means 15 to move to the left in FIG. 6. Although the support means 15 may be fixed rigidly, it is assumed here to be connected to the carriage 14, for example by means of a rod 612 (FIG. 6). As beforementioned, when the carriage 14 is displaced, the support means 13, which is coupled to the carriage via the ball joint 131, will also be displaced. Rotation around the horizontal axis H—H is effected by manipulating the lever 182, so as to engage the crank 181 with the steel-wire of a Bowden-cable 192. The free end of the steel-wire in the Bowden-cable 192 is connected to a lug or like device 193 on the table 605. As the steel-wire is drawn downwards in FIG. 6, the edge of the table 605 lying nearest the viewer will swing downwards about the axle-stubs 606 and 607, while when the steel-wire in the Bowden-cable 192 is moved upwards, the table will be swung in the opposite direction. The support means 14 and 15 will also be swung, together with the table 605, about the horizontal axis H—H.

Figure 7:
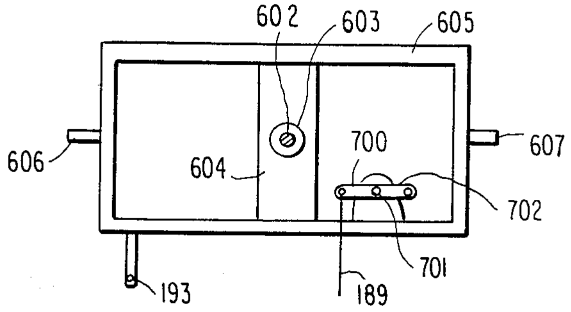
FIG. 7 is a sectional view of the apparatus illustrated in FIG. 6, taken about lines VII—VII.

The third movement, involving rotation about the vertical axis V—V, is effected by manipulating the lever 184 (FIG. 1), to engage the crank 181 with the inner steel-wire of a third Bowden-cable 189. The free end of the steel-wire of this Bowden-cable 189 is connected to one arm 700 of a double-arm lever, which is journalled at its center on a pin 701 firmly mounted on a bracket on the frame 605. The other arm 702 of the double-arm lever is rotatably connected to a pin 703 mounted on the plate 600. As will be seen from FIG. 7, when the lever 700–702 is turned clockwise, the plate 600 is rotated clockwise about the central stud 602. It will be obvious that the steel-wire in the cable 189 cannot be connected directly to the plate 600 rotatably mounted on the central stud 602, and that the use of a double-arm lever enables movement of the steel-wire to be transmitted to the plate.

Many modifications are conceivable within the scope of the following claims. For example, the apparatus according to FIG. 4 can be modified by arranging beneath the means 13 for supporting the small of the back a moveable, wedge-like member, the position of which horizontally can be controlled in dependence upon said pressure. In this way, the support means 13 abutting the inclined surface of the wedge-like member is imparted a pressure, adapted to suit the patient.

It has been found extremely important in respect to the treatment programme to correctly correlate traction, torsion and distortion with the control of the height of the means for supporting the small of the back, so that the pressure against said means is the correct pressure for the treatment in process. This pressure may be constant (which in itself may require adjustment to the height of the support means 13) or may vary in accordance with a predetermined programme, which programme may, in turn, be selected individually for a special patient or may be intended for a group of patients exhibiting a number of similar back deficiences. It is only by means of this combined treatment that a realistic basis for the treatment can be obtained, where it is known what manipulations must be carried out and carrying out these manipulations at the correct location and at the correct time. The apparatus according to the invention enables such treatment to be carried out in practice in an efficient manner.

I claim:

1. An apparatus for treatment of back ailments of a patient, comprising:

a support means (10) for supporting a patient in a horizontal, lying position;

a first tension force take-up means (26), arranged to pass around the pelvis of the patient;

a second tension force take-up means (19), arranged to pass around the chest of the patient;

pulling or tension means (17) connected to one of the two tension force take-up means (26) and arranged to move the same relative to the support means (10);

a readily moveable carriage means (14) for movement relative to the support means (10), with but slight friction, for carrying either the pelvis or chest of the patient and exhibiting a high degree of friction against the associated tension force take-up means (26);

and a moveable means (13) for supporting the small of the patient's back, and wherein the readily moveable carriage means (14) comprises means for executing, independently of translatory movement of said carriage means (14) relative to the support means (10), rotary movement substantially in the horizontal plane and a skewing movement about an axis extending substantially parallel to the longitudinal direction of the carriage means (14), in accordance with a predetermined program.

2. The apparatus according to claim 1, wherein the readily moveable carriage means (14) supports the pelvis of the patient and comprises means for executing rotary movement about a substantially vertical axis located between said carriage means (14) and the means (13) for supporting the small of the patient's back located adjacent said moveable carriage means (14).

3. The apparatus according to claim 2, wherein the readily moveable carriage means (14) comprises means for executing a skewing movement about a substantially horizontal axis.

4. The apparatus according to claim 1, wherein the readily moveable carriage means (12) supports the chest of the patient and comprises means for executing rotary movement about a substantially vertical axis located between a fixed carrier means (14) supporting the pelvis of the patient, and the means (13) for supporting the small of the back located adjacent the fixed means (14).

5. The apparatus according to claim 4, wherein the readily moveable carriage means (12) and the means (13) for supporting the small of the back comprises means for executing skewing movement about a substantially horizontal axis.

* * * * *